US005300111A

United States Patent [19]
Panton et al.

[11] Patent Number: 5,300,111
[45] Date of Patent: Apr. 5, 1994

[54] TOTAL ARTIFICIAL HEART

[75] Inventors: Ronald L. Panton, Austin; William V. Healey, Boerne, both of Tex.

[73] Assignee: Pyxis, Inc., San Antonio, Tex.

[21] Appl. No.: 830,051

[22] Filed: Feb. 3, 1992

[51] Int. Cl.$^5$ .............................................. A61M 1/10
[52] U.S. Cl. ........................................................ 623/3
[58] Field of Search ........................... 623/3; 600/16–18

[56] References Cited

U.S. PATENT DOCUMENTS

| | | | |
|---|---|---|---|
| 3,842,440 | 10/1974 | Karlson . | |
| 3,874,002 | 4/1975 | Kurpanek | 137/527 X |
| 4,173,796 | 11/1979 | Jarvik | 417/389 X |
| 4,213,207 | 7/1980 | Wilson . | |
| 5,006,104 | 4/1991 | Smith et al. | 623/3 X |
| 5,011,380 | 4/1991 | Kovacs . | |
| 5,064,353 | 11/1991 | Tsukahara | 623/3 X |
| 5,066,300 | 11/1991 | Isaacson et al. | 623/3 |
| 5,089,016 | 2/1992 | Millner et al. | 623/3 |
| 5,089,018 | 2/1992 | Lapeyre et al. | 623/3 |
| 5,139,516 | 8/1992 | Mogendovich | 623/3 |
| 5,145,333 | 9/1992 | Smith | 623/3 X |

FOREIGN PATENT DOCUMENTS 0239723 10/1986 Fed. Rep. of Germany ........ 600/16

OTHER PUBLICATIONS

Raj, Bonvouloir and Moskowitz, "Ferrofluid as an Acoustical Design Parameters" 1991, Audio Engineering Society, Reprint 3195 (G-5), 7M/G-5.
Cathey, J. J., Topmiller, D. A. & S. A. Nasar, "A tubular self-synchronous motor for artificial heart pump drive," 1986, IEEE, BME-33, p. 315.
Yang, C. H., & S. A. Nasar, "A permanent magnet linear oscillatory motor for the total artificial heart," Elect Mech & Power Sys, 1988, 15, p. 381.

Primary Examiner—Randall L. Green
Assistant Examiner—Elizabeth M. Burke

[57] ABSTRACT

A totally implantable artificial heart with two ventricles is disclosed. The blood is pumped alternately from each ventricle using a linear electric motor that moves an armature to push the movable walls of the ventricles. The motor may be made small, and hence light, if it is electrically inefficient. Excess heat is transferred by the convective motion of a heat transfer fluid through special passages in the motor and by effective conduction paths designed into the elements. The motion of the heat transfer fluid is engendered by the movable walls that at the same time are performing the pumping action.

15 Claims, 11 Drawing Sheets

TOTAL ARTIFICIAL HEART

BACKGROUND

1. Field of Invention

The present invention relates to an improved pump and actuator for a totally implantable artificial heart.

2. Description of Prior Art

Heretofore a total artificial heart has not been implanted in a human being. As of November 1991 there have been 220 partial artificial hearts implanted. These hearts are partial in the sense that tubes come out of the patient's chest and are connected to a console that provides compressed air to actuate the heart. It is of course a great disadvantage for a patient to be tethered to a large machine. Not only is mobility restricted, but the tubes piercing the patient's chest are a route for infection to enter.

Currently the National Institutes of Health (NIH) has four programs to develop a totally implantable artificial heart that use an electric motor ("Proceedings Cardiovascular Science and Technology Conference," December, 1991, Bethesda Md., published by Association for the Advancement of Medica Instrumentation, Arlington Va.). It is envisioned that the patient will wear a belt of batteries that feed electricity to a coil on the outside of the patients skin. Another coil implanted internally will pick up the electric energy for use by the artificial heart. Thus, there are no wires or tubes that break the skin and provide a dangerous route for infection. A circuit implanted in the patient conditions and controls the electricity that is then passed on the electro-mechanical artificial heart (the pump and actuator). The pump-actuator is the subject of this patent. All of the pump-actuator designs in the NIH programs use electric motors that rotate. Because the pumping action is a linear motion it is necessary to have a mechanism to change the rotary motion to a linear motion. This adds size, weight, and especially complexity to the device. The rotary motor also must have a commutation mechanism, a further complexity.

An extremely important quality of a total artificial heart is its reliability. Repair or adjustment on an implanted heart is difficult and failure is catastrophic. It is a truism that simple machines are more reliable and that complex machines with many parts have greater possibilities for failure. Hence, the complexity of the rotary-to-linear mechanism is an inherent disadvantage with regard to reliability.

Another characteristic of importance is the weight of the artificial heart. The lowest published weight for designs in the NIH program is 671 grams. The designers have noted that these artificial hearts are suitable only for a person who weighs over 150 pounds. For comparison, a diseased natural heart may be 350 grams, an average man's heart 312 grams, and an average woman's heart only 250 grams. A patient may tolerate some extra weight, however, it is apparent from these numbers that it would be a great advantage if future artificial hearts were much lighter.

Linear electric motors are very attractive for artificial hearts as they eliminate the rotary-to-linear motion conversion mechanism. Also, because linear motors have substantially fewer parts, one expects increased reliability over rotary motors and their associated rotary-to-linear mechanisms. Several types of linear motors have been proposed previously for artificial hearts: U.S. Pat. No. 3,842,440 to Karlson (1974); U.S. Pat. No. 3,874,002 to Kurpanek (1975); articles by Yang, C-H, and Nassar, S. A., "A Permanent Magnet Linear Oscillatory Motor for the Total Artificial Heart," Electric Machines and Power Systems, Vol.15, p 381,1988; and by Cathey, J. J., Topmiller, D. A., and Nasar, S. A., "A Tubular Self-Synchronous Motor for Artificial Heart Pump," IEEE Transactions on Biomedical Engineering, BME-33, No. 3, March 1986. None of these proposed linear motors have yielded a practical artificial heart because by using standard design principles they turn out to be too large and heavy.

The efficiency of a linear motor of given output power is dependent upon the size, the bigger the motor the more efficient it is. Thus, to have a linear motor small enough for the application to an artificial heart it must be an inefficient design. This is contrary to instinct and custom. In the present invention the excess heat of a small inefficient motor is transferred to the blood by specific elements incorporated into the design for that purpose.

Depending on how they are categorized there are about five types of linear electric motors. Within each category many variations of internal arrangements for the electrical parts, that is magnets, coils, magnetic circuit material, et. cetera., are possible and are well-known to experts in the field of linear motors. The present invention is not limited to a particular type or configuration of linear motor. Indeed the principles also apply to rotary electric motors. Further objects and advantages of the invention will become apparent from consideration of the drawings and ensuing description.

SUMMARY

Reliability, long life, and small weight are the key characteristics of an artificial heart. A simple, durable, linear motor may be made small enough for use in an artificial heart if, as described in this invention, active and purposeful removal of excess heat is effected. Furthermore, there is adequate input power available and adequate capacity to reject unused power as heat. Contrary to custom a high efficiency is not desired, especially at the price of a large, heavy, and complicated machine based on a rotary motor.

Accordingly, several objects and advantages of the present invention are to provide a practical artificial heart with a linear electric motor, and to provide an artificial heart that is simple with few parts, especially moving parts, and thereby increased reliability and durability. Further objects are to provide an artificial heart that is light in weight, with slow moving parts, quiet operation, and one that is easily controlled.

The invention includes left and right ventricle chambers having movable walls that are actuated by a linear electric motor contained in a housing that connects the ventricles. The size and weight of the motor is substantially reduced by employing elements for the purposeful transfer of excess heat from the motor to the blood. Heat conduction paths are made efficient and/or convection employing a heat transfer fluid is utilized. The linear motor is submerged in the heat transfer fluid and flow paths for the heart transfer fluid are included through and over the motor. The motion of the ventricle walls that pumps the blood also engenders the flow of the heat transfer fluid through the motor.

DESCRIPTION OF PREFERRED EMBODIMENTS

Other components, not the subject of this invention, are assumed to transport the electricity into the patient and provide the control thereof. The proper electricity will be assumed to be delivered to the electro-mechanical artificial heart.

Figure 1:
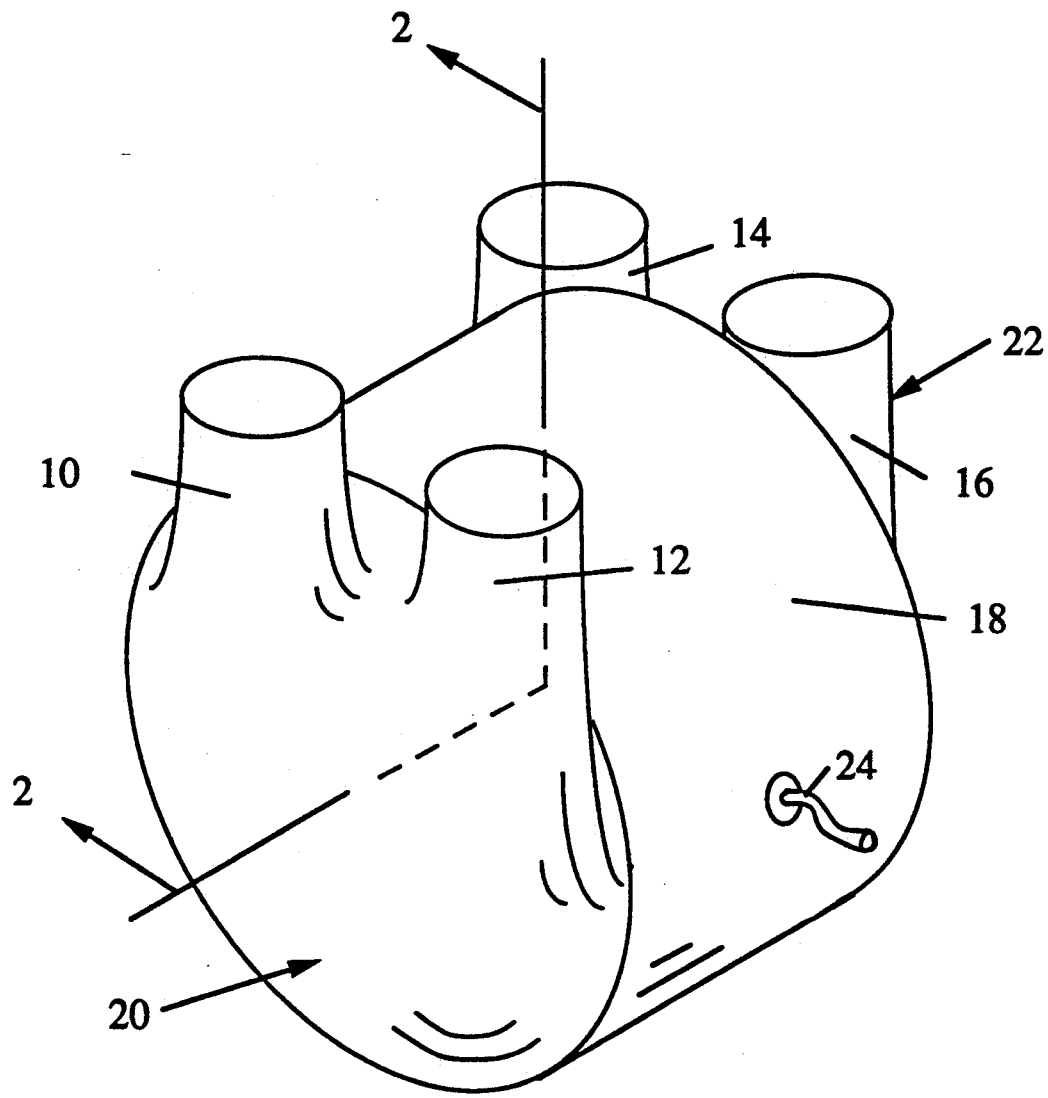
FIG. 1 is an isometric view of a total artificial heart according to the present invention.

FIG. 1 shows a perspective view of the artificial heart. The blood comes in from the body through an inlet port 10 and goes out to the lungs through an outlet port 12. An inlet port 14 receives blood from the lungs and blood is sent out to the body through an outlet port 16. A generally cylindrical central housing 18 connects a right ventricle housing 20 and a left ventricle housing 22. Electric power is supplied through an electric cable 24 that connects to a separate source.

Figure 2:
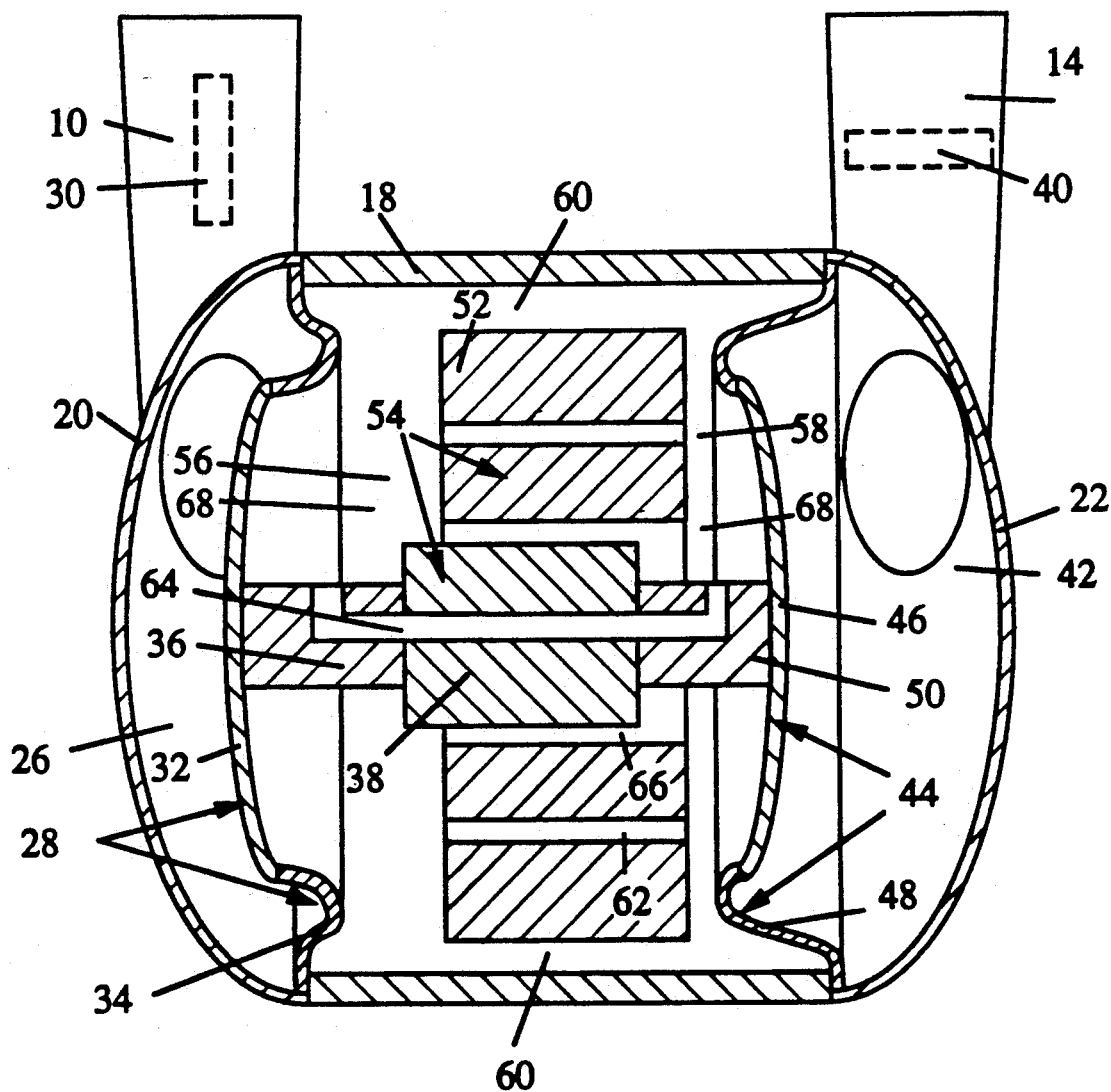
FIG. 2 is a cross-sectional view of the total artificial heart, taken in the first position, along line 2—2 of FIG. 1 and showing the two pusher plates.

FIG. 2 shows the preferred embodiment where a right ventricle cavity 26 is formed by the right ventricle housing 20 and a right movable wall shown generally at 28. Depicted in FIG. 2 as hidden is an entrance valve 30 inside the inlet port 10. Heart valves that are customarily implanted in living hearts are well-developed and suitable for use in this application. The corresponding exit valve is in the half of the heart that has been cut away. The right movable wall 28, comprising a right pusher plate 32 and a right flexible seal 34, is connected to a right armature extension 36. The armature extension 36 is connected to a linear electric motor armature 38. The inlet port 14 also contains a left inlet valve 40. A left ventricle cavity 42 is formed by the left ventricle housing 22 and a left movable wall shown generally at 44. The movable wall 44 includes a left pusher plate 46, and a left flexible seal 48; the pusher plate being connected to armature 38 by a left armature extension 50. The pusher plates 32 and 46 are circular and curved, with their concave sides against the armature extensions 36 and 50, respectively. The pusher plates are approximately 6 centimeters (2.5 inches) in diameter and are maintained generally concentric with the cylindrical housing 18 by the seals 34 and 42 respectively.

For the effective transfer of heat, a material of high thermal conductivity, such as metal, is desirable for portions of the pusher plates and armature extensions. The sides of the pusher plates facing the ventricle cavities 26 and 42, respectively, and contacting the blood may have a coating of material that will prevent clotting of the blood.

A stator 52 of a linear electric motor shown generally at 54 and includes the armature 38, is connected to the housing 18. For the effective removal of heat, a material of high thermal conductivity, such as metal, is desirable for portions of the stator 52 that connect to the housing 18 and for the housing 18 itself. The motor 54 generally divides the region within the housing 18 and between the walls 32 and 46 into a right reservoir 56 and a left reservoir 58. the two reservoirs 56 and 58 may be connected together by one or more flow passages through or around the motor 54. For example, one or more flow passages 60 may be provided between the motor 54 and the housing 18. One or more flow passages 62 (two are shown) may be provided along the interior of the stator 52. The armature 38 and the armature extensions 36 and 50 are shown broken by a continuous flow passage 64 that opens into reservoirs 56 and 58 through the sides of the armature extensions. Also, one or more flow passages may be provided by space 66 between the stator 52 and the armature 38. The reservoirs 56 and 58 and the various flow passages connecting the reservoirs are filled with a heat transfer fluid 68. The heat transfer fluid takes heat from the motor and transports it to the reservoirs and the reservoir walls. The fluid is preferably a liquid of high thermal conductivity. Passages with rough, striated, or enhanced heat transfer surfaces as described in "Techniques to Augment Heat Transfer," by A. E. Bergles in Handbook of Heat and Mass Transfer. McGraw-Hill Book Company, 1988) may be employed.

Figure 4:
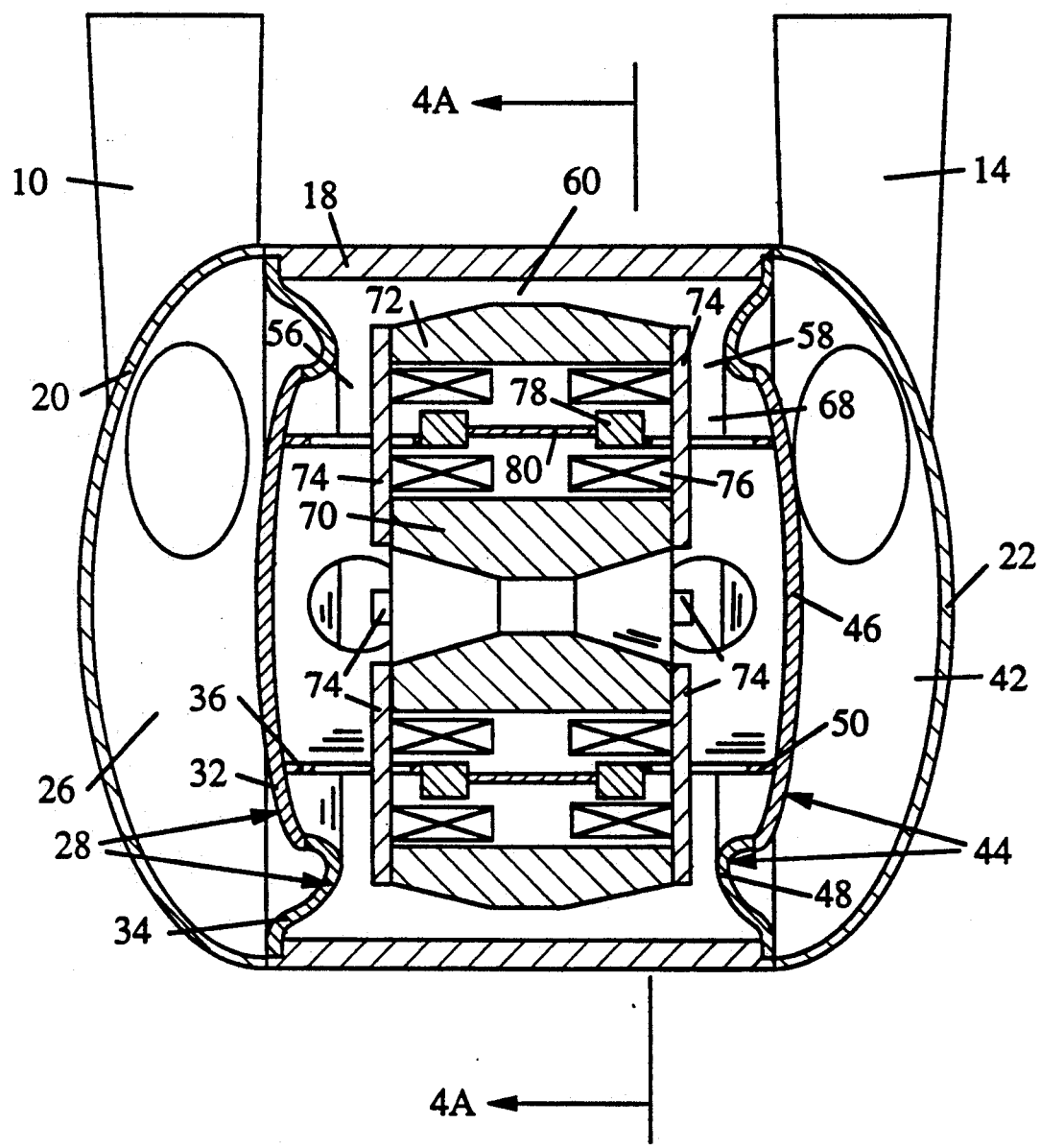
FIG. 4 is a view similar to FIG. 2 but showing an embodiment of the present invention having a linear motor of the double-voice-coil configuration.

FIG. 4 shows a specific embodiment for the linear electric motor that may be called a double moving-magnet voice coil motor. The electrical arrangement for this motor is described in "Design and Fabrication of a Long-Life Stirling Cycle Cooler for Space Application," Phase III Final Report for the period September 1981–September 1990 from Philips Laboratories, North American Philips Corporation to NASA, Goddard Space Flight Center, August 1990, C. Keung, P. J. Patt, M. Starr, R. C. Sweet, L. A. Bourdillion, R. Figuerola, M. Hartman, R. McFarland. The stator of the motor includes an inner stator pole piece 70 and an outer stator pole piece 72, both of magnetic material, connected by a plurality of supports 74 of nonmagnetic material, and four electric wire coils 76. The armature includes two cylindrical ring permanent magnets 78 that are radially magnetized, being attached together by a connection piece 80 that is made of nonmagnetic material. This figure shows the armature extensions 36 and 50 as a cylindrical shapes connecting the magnets 78 and the pusher plates 32 and 46. The armature extensions also have several holes which the supports 70 pass through. A second purpose for the holes is to allow the heat transfer fluid 68 to redistribute as the armature moves.

Cross-section view 4A depicts the arrangement of the parts of the linear motor described above and specifically shows flow passage 60 over the stator, flow passages 62 through the stator, flow passages 66 between the stator and the armature. Each flow passage has been formed by partitioning an annular area into four sections. The number of sections employed is arbitrary. In cross-section view 4B—4B a variation is shown where an impeller 82 is attached to and moves with the magnet connection piece 80. The impeller forces the heat transfer fluid to move through the flow passages 62 and 66. Other features of this embodiment are similar to FIG. 2.

Figure 5:
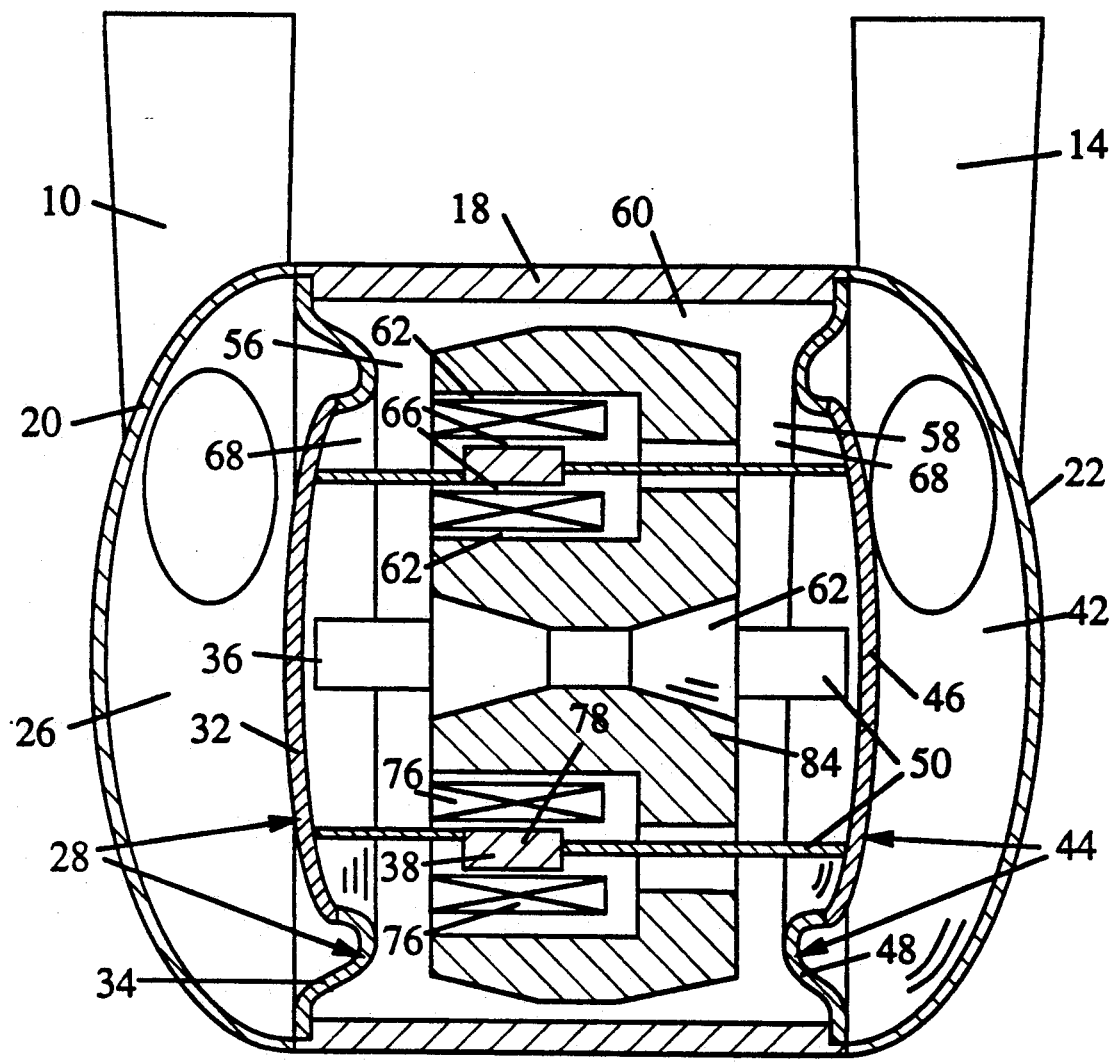
FIG. 5 is a view similar to FIG. 2 but showing an embodiment of the present invention having a linear motor of the moving-magnet voice-coil configuration.

An alternate preferred embodiment is shown in FIG. 5 in a cross-section view similar to FIG. 4. Here a single moving-magnet voice coil linear motor is shown. This motor is also described in "Design and Fabrication of a Long-Life Stirling Cycle Cooler for Space Application," Phase III Final Report for the period September 1981–September 1990 from Philips Laboratories, North American Philips Corporation to NASA, Goddard Space Flight Center, August 1990, C. Keung, P. J. Patt, M. Starr, R. C. Sweet, L. A. Bourdillion, R. Figuerola, M. Hartman, R. McFarland. In this motor a single stator pole piece 84 is used together with one permanent magnet 78 and two coils 76. In this embodiment the magnetic flux circuit is returned from the outer pole to the inner pole through the continuous path of the stator piece 84. Note that flow paths 66 and 62 merge within the motor and continue as a combined flow path. The armature extensions 36 and 50 shown in FIG. 5 are simply four rectangular struts. Other features of this embodiment are similar to FIG. 2.

Figure 6:
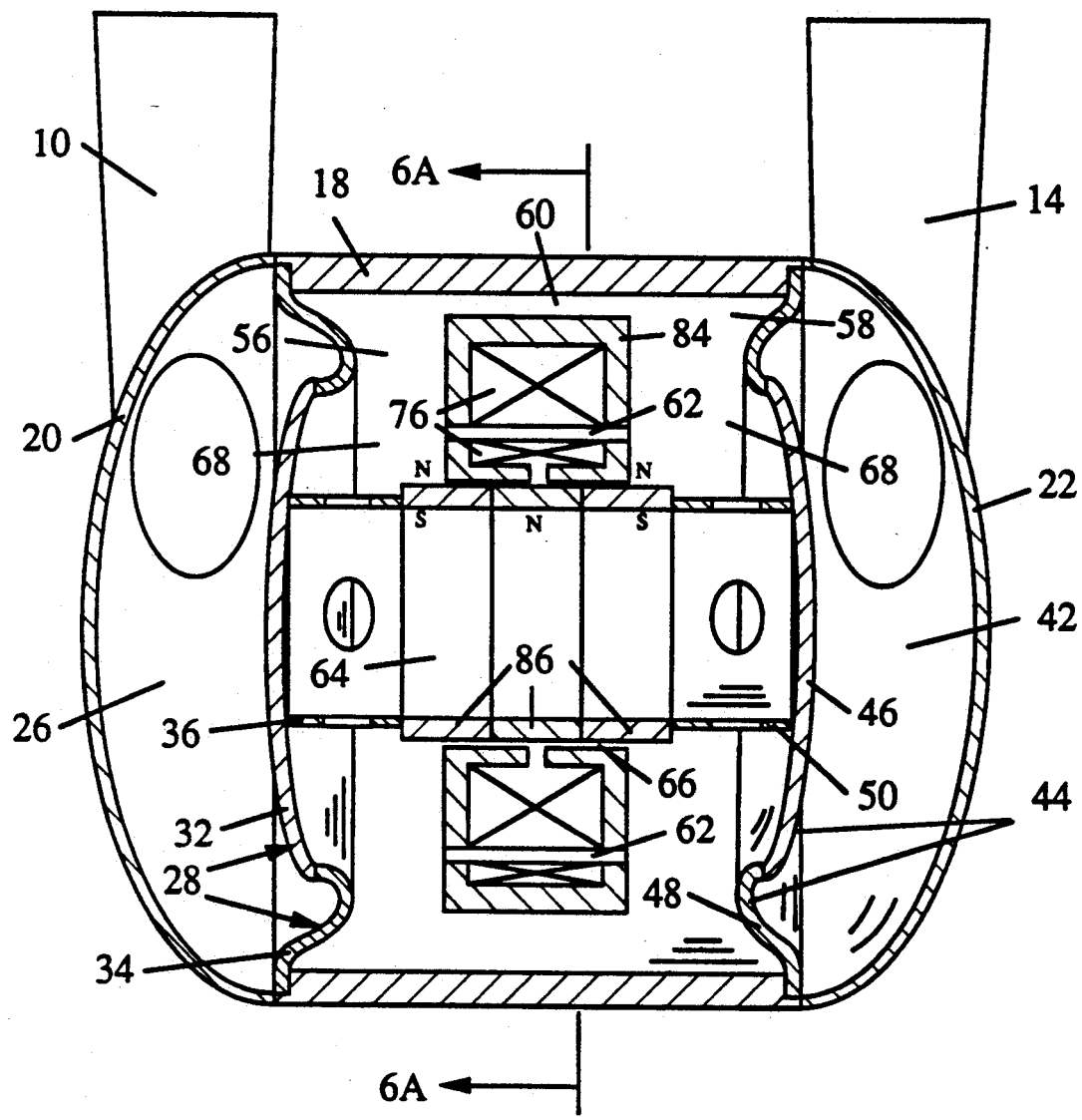
FIG. 6 is a view similar to FIG. 2 but showing an embodiment of the present invention having a linear motor of a non-commutated direct-current configuration.
Figure 6A:
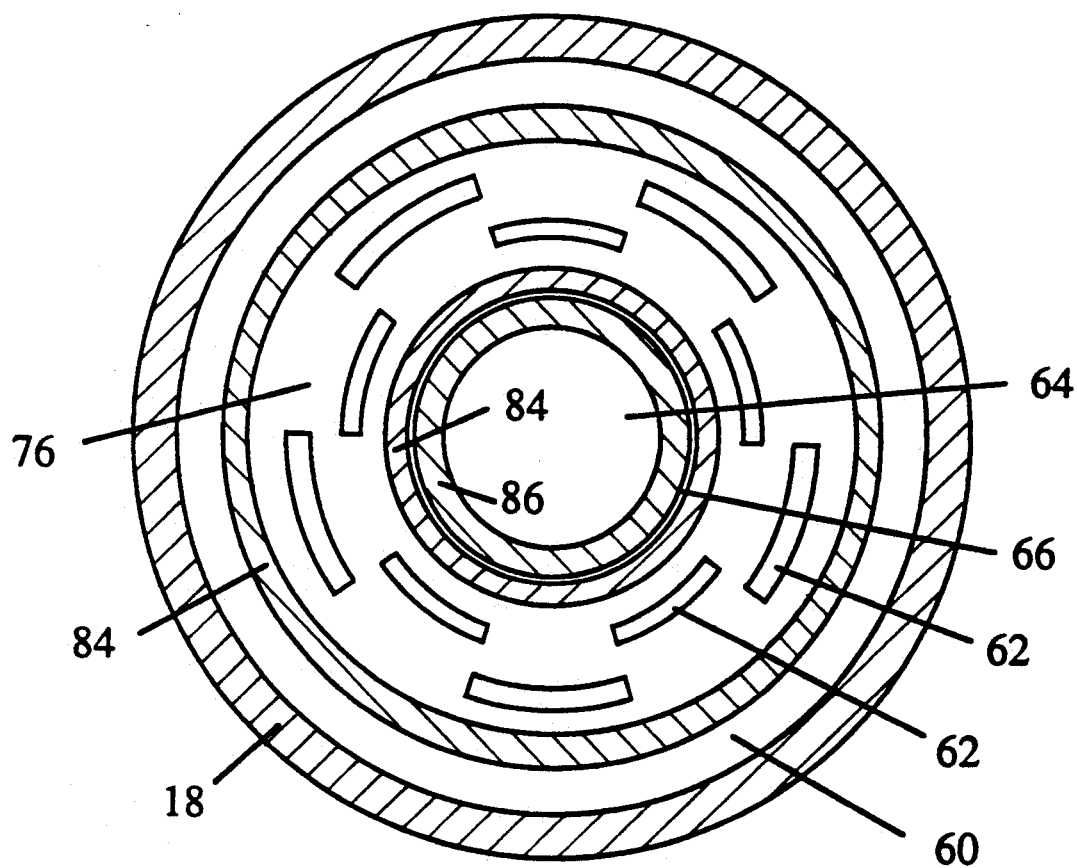
FIG. 6A is a cross-section, taken along line 6A—6A of FIG. 6, and showing the cooling flow passages of the linear motor.

An alternate preferred embodiment is shown in FIG. 6 in a cross-section view similar to FIG. 4. In this embodiment the armature consists of three ring magnets 86 placed stacked together in line. The direction of magnetization is radial and alternates for each magnet (not shown in the figure). The armature extensions 36 and 50 are cylindrical shapes with holes the same as those of FIG. 4. The holes in the armature extensions 36 and 50 allow heat transfer fluid 68 to move into the passage 64 through the armature. In this motor a single stator pole piece 84 is used and encloses a single coil 76. Flow paths 62 have walls that are formed of nonmagnetic material and pass through the stator piece 84 and the coil 76. In FIG. 6A flow paths 62 are shown as segments of an annular cylinder. The paths 62 are chosen and spaced so that every radial section of the coil area 76 has the same area for the winding of wires. Other features of this embodiment are the same as those of FIG. 2.

Figure 7:
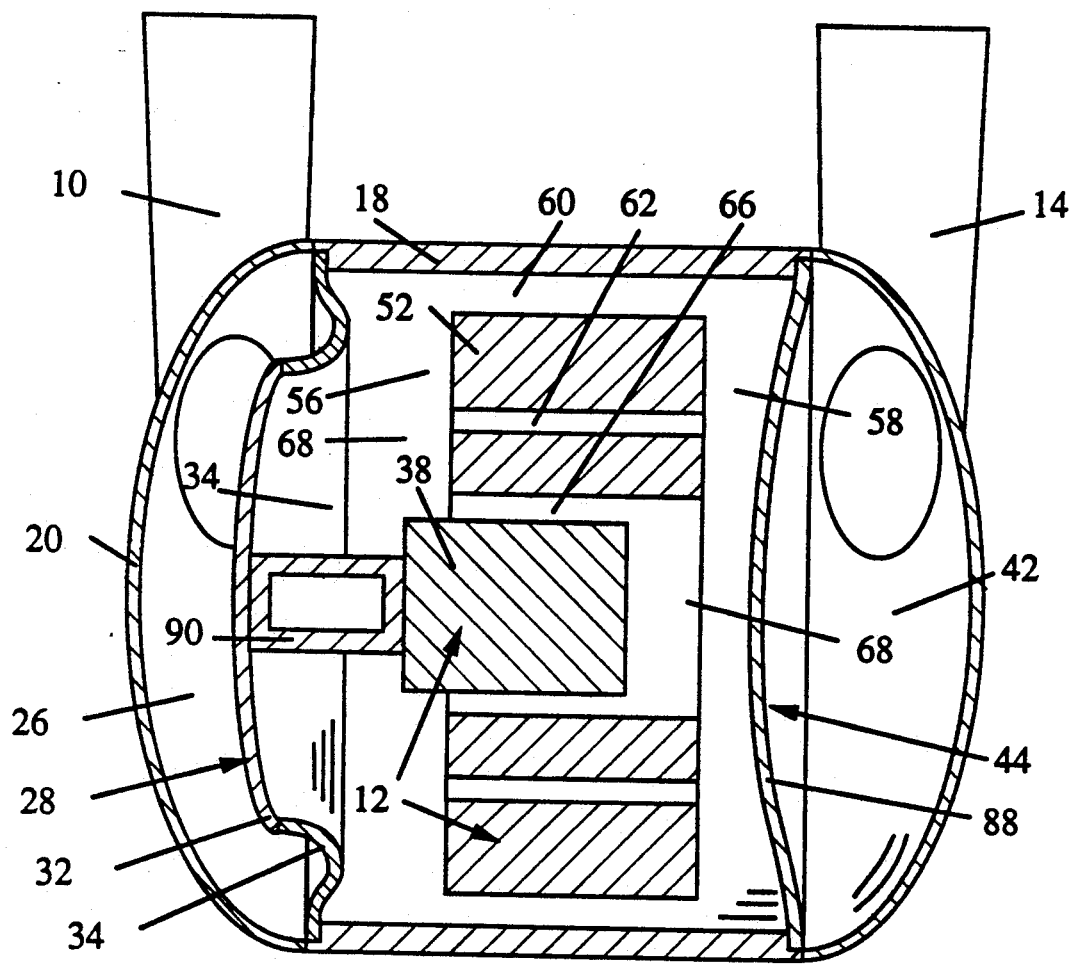
FIG. 7 is a view similar to FIG. 2 but showing an embodiment of the present invention having one pusher plate and one diaphragm.

Another embodiment is shown in FIG. 7 where the left ventricle flexible wall 44 is a left diaphragm 88. In this case the heat transfer fluid 68 also acts as a pressure transfer fluid. Pressures generated at the movable wall are transferred through the fluid 68 to act on the diaphragm 88. The armature 38 has a single extension and this embodiment also exemplifies the use of a heat pipe 90 as the armature extension. Heat pipes can have effective thermal conductivities several hundred times larger than a metal of the same cross-section. Heat pipes are well-known to those skilled in the art of heat transfer and the principles of operation may be understood by reference to Winter, E. R. F., and Barsch, W. O., "The Heat Pipe," *Advances in Heat Transfer*, Vol. 7 (T. F. Irvine Jr. and J. P. Hartnett, eds.), Academic Press Inc., New York, 1971. Other features of this embodiment are the same as those of FIG. 2.

Figure 8:
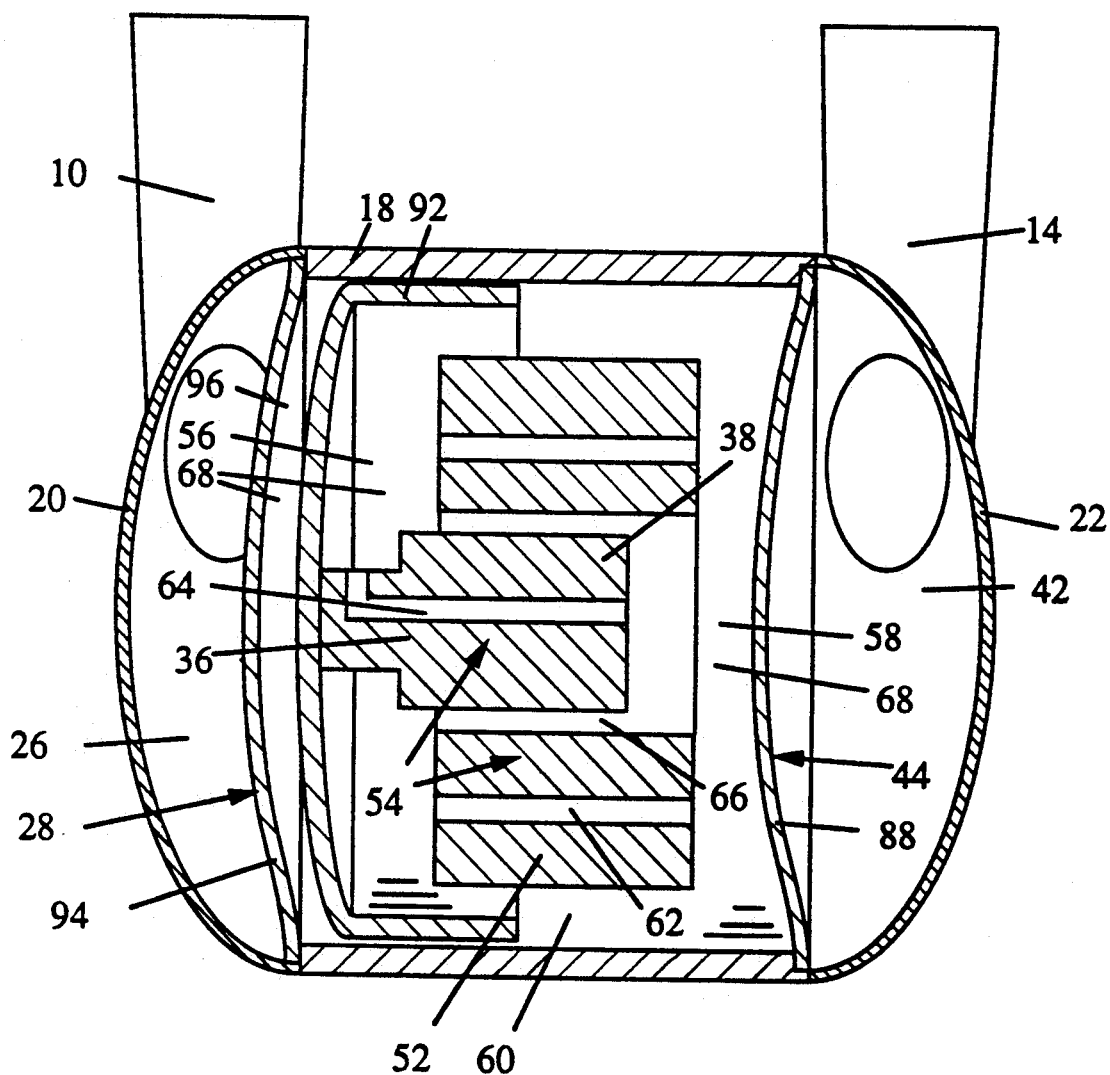
FIG. 8 is a view similar to FIG. 2 but showing an embodiment of the present invention having a piston and two diaphragms.

In another alternate embodiment, shown in FIG. 8, a piston 92 is connected to the single armature extension 36. The left ventricle movable wall 44 is flexible diaphragm 88 and the right ventricle movable wall 28 is a flexible diaphragm 94. A cavity 96 is the space between the diaphragm 94 and the piston 92. Reservoir 56 is between piston 92 and linear motor 54 and reservoir 58 is between linear motor 54 and diaphragm 88. The heat transfer fluid 68, being at the same time the pressure transfer fluid, occupies the cavity, the reservoirs and the flow passages. Housing 18 serves as a cylinder for the piston. Other features of this embodiment are the same as those of FIG. 2.

OPERATION OF PREFERRED EMBODIMENTS

The largest force that an electric motor of given size can produce is determined by the current in the coils. In turn, the current is limited by the highest temperature allowed for the wire material. Thus, the conclusion is that to get the most force and power from a given size motor, one must actively and purposefully remove the heat from the coils. Another viewpoint is that a motor of given power can be made smaller if one actively removes heat from the coils. However, this active removal of heat also makes a less efficient motor.

On the other hand, linear electric motors are more efficient when they are larger. This leads to conflicting requirements; the artificial heart needs a small linear motor, but small linear motors are inefficient. Therefore, in order to gain the inherent simplicity and reliability of a linear motor, which at the same time is small enough to be used in an artificial heart, one must be prepared to sacrifice efficiency. This goes against the common belief that high efficiency is good. In the NIH artificial heart program the "request for proposal" document stated that an overall efficiency of 25% or greater was desirable (Request for Proposal No. NHLBI-HV-86-02. National Heart Blood and Lung Institute, Jan. 15, 1986).

In the total artificial heart application about 1.2 to 2.5 watts of pumping power are required. In order to assess that an inefficient motor is feasible for the total artificial heart application one must consider two things: the input power available and the ability to reject unused energy as heat. Sufficient input power is available because present systems to transfer electric power across the skin have a much greater capacity than is needed; one NIH design can transfer 70 watts of energy. Energy that is removed from the motor as heat is ultimately transferred to the body, especially to the blood that leaves the heart. Estimates show that there is more than adequate capacity for the body to receive this heat with negligible increase in the blood temperature and thus without unwanted medical consequences. From the standpoint of the artificial heart application there is adequate input power available and adequate capacity to reject unused power as heat. Contrary to custom a high efficiency is not desired. However, a practical artificial heart design needs to have elements that actively transfer the excess heat energy from the electric coils, where it first appears, to the ventricles where the blood will take it away.

Figure 3:
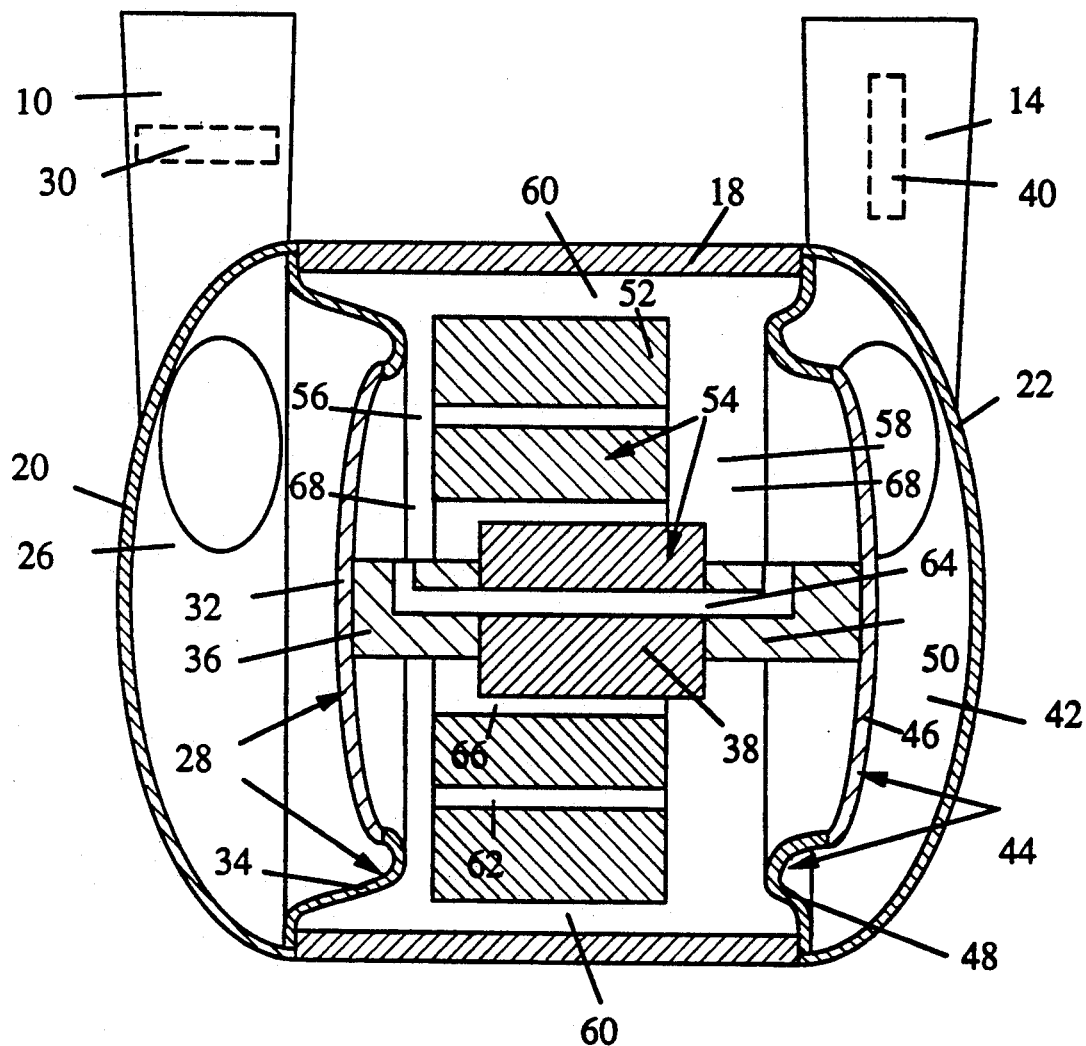
FIG. 3 is a view similar to FIG. 2 but showing the two pusher plates in a second position.

The operation of the artificial heart is best described with reference to FIG. 3. Assume electricity is supplied by other components so that that linear motor 54 is energized to push the armature 38 and movable wall 28 to the left. This causes the volume of the right ventricle 26 to decrease. Inlet valve 30 in inlet port 10 is closed and the corresponding outlet valve, not shown as it is on the side that is cut away, is open allowing blood to be pumped to the lungs. Artificial heart valves operate automatically without the need for any other agent. Simultaneously, the moving armature 38 causes movable wall 44 of the left ventricle 42 to move to the left and increase the ventricle volume. Inlet valve 40 is open and the left ventricle 42 fills with blood from the lungs. When the linear electric motor 54 is energized with current in the opposite direction so as to move armature 38 to the right, the opposite direction, right ventricle 26 fills and left ventricle 42 pumps blood to the body. In this phase inlet valve 30 for the right ventricle 26 is open and valve 40 for the left ventricle 42 is closed as shown in FIG. 2. This alternate pumping from right and left ventricles is unlike the natural heart, however, medical opinion is that alternate pumping is completely acceptable.

Figure 4A:
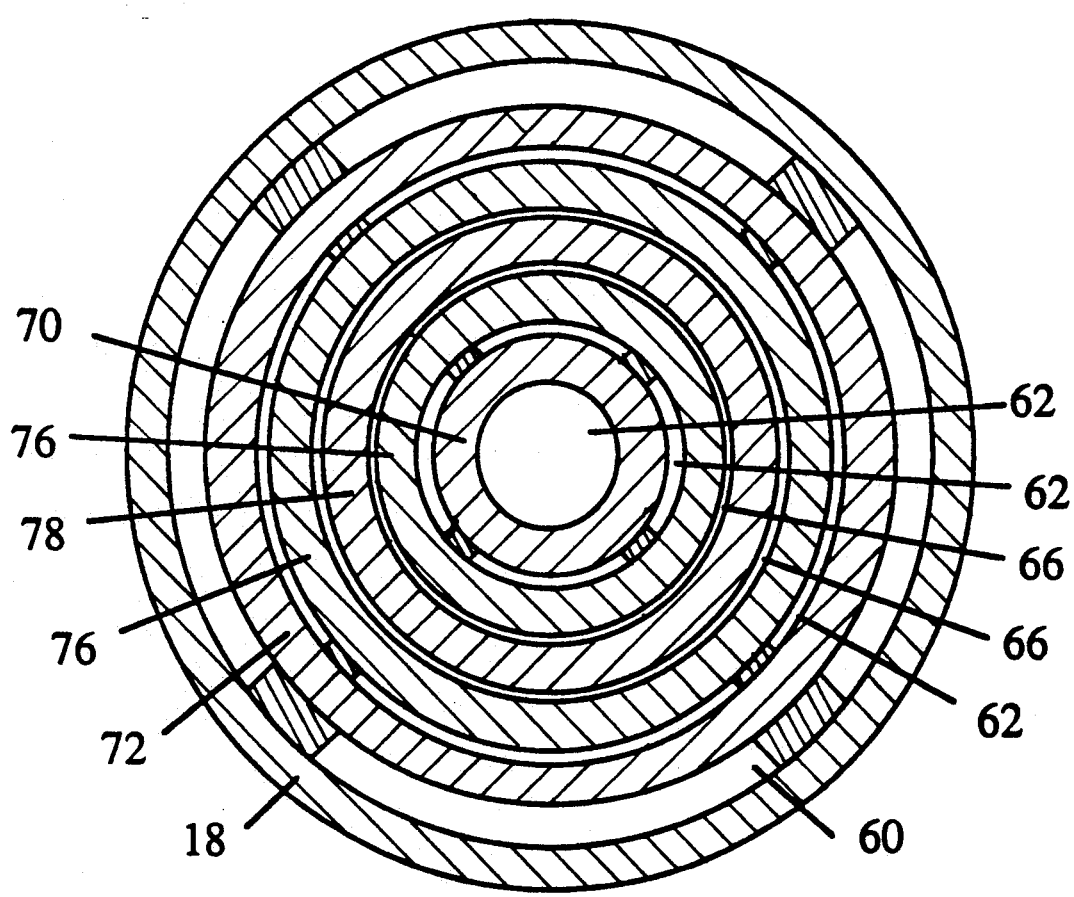
FIG. 4A is a cross-section, taken along line 4A—4A of FIG. 4, and showing the cooling flow passages of the linear motor.
Figure 4B:
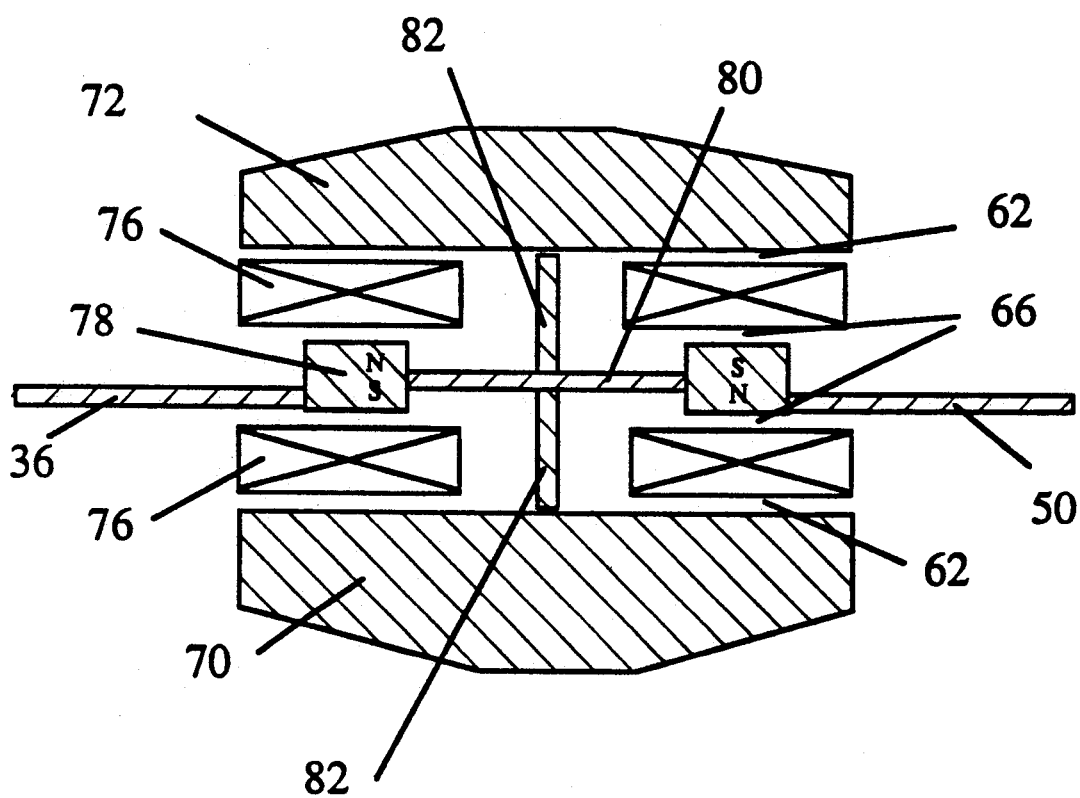
FIG. 4B is a fragmented view of the motor of FIG. 4 showing a variation with an impeller attached to the armature.

To purposefully remove heat from the linear motor and transfer it to the blood and to the surrounding body tissue, two modes of heat transfer are practical: conduction and convection. One heat conduction path is along armature 38 and the armature extensions 36 and 50 and into pusher plates 28 and 44 and hence subsequently into the blood. Selecting materials of high thermal conductivity, including metals, and providing heat conduction path cross-sectional areas that are substantial will promote heat conduction. Another heat conduction path is from the stator 52 through its connection (illustrated in FIG. 4A) to housing 18. The housing 18 transfers heat to the body tissues in which it is in contact and also conducts heat to the ventricle housings 20 and 22 where the heat is transferred to the blood. The blood leaving the pump carries the heat to the lungs and skin where it is rejected to the environment.

Removal of heat by the convection mode involves the motion of fluid past the hot regions. Natural convection utilizes the motion induced by buoyancy of heated fluid and is not nearly as effective as forced convection, used in the present invention, where the fluid motion is forced. Refer again to FIG. 2 and assume that the armature 38 is moving to the right. The entire region between movable walls 28 and 44, that is reservoirs 56 and 58 and flow paths 60, 62, 64, and 66, is filled with heat transfer fluid 68. In general liquids have better physical properties for use as heat transfer fluids than do gases. The moving wall 28 creates a pressure in reservoir 56 that is greater than that created in reservoir 58 by the motion of moving wall 44. This pressure difference causes the heat transfer fluid 68 to flow over the parts of the linear motor through the various flow passages. As the heat transfer fluid 68 flows over the surfaces of the passages it receives heat from the walls of the flow passages. When the heat transfer fluid 68 exits the flow passages into reservoir 58 the fluid mixes with the fluid already within the reservoir. Finally, the fluid within the reservoir transfers heat to the movable wall 44 where conduction through the wall deposits the heat into the blood.

At the end of the stroke to the right, the armature 38 stops in preparation to begin moving in the opposite direction. Heat transfer fluid, fresh cool fluid from reservoir 56, has just been brought in to occupy the several flow passages by the previous stroke. The heat transfer fluid 68 also stops and during this period of slow or no motion heat is conducted into the fluid occupying the passages. On the return stroke the heated fluid in the passages is washed out into reservoir 56 and further fluid from reservoir 58 cools the passage walls as it flows through. As the fluid exits into reservoir 56 it mixes with fluid already there. Once again the fluid within the reservoir transfers heat to flexible wall 28 where conduction deposits the heat into the blood.

Thus, the armature motion not only pumps the blood but at the same time it engenders the motion of the heat transfer fluid that cools the linear motor. Two somewhat distinct processes occur. First, conduction heats the fluid within the passages while there is slow or no motion at the end of a stroke and then that fluid is washed out into the reservoirs. Second, some fluid moves completely through a passage as the stroke progresses and in so doing it receives and transports heat by convection.

One skilled in the art of heat transfer can optimize the volumes, areas, and lengths of reservoirs 56 and 58 and flow passages 60, 62, 64, and 66 in order to achieve the proper heat transfer for a motor of known dimensions and efficiency. Other refinements can be used on the walls of the flow passages to improve the heat transfer. These refinements, for example striations or roughness, are collectively known as 'enhanced heat transfer surfaces' and are described in the article "Techniques to Augment Heat Transfer," by A. E. Bergles in *Handbook of Heat and Mass Transfer*. McGraw-Hill Book Company, 1988.

The embodiments shown in FIGS. 4, 5, and 6 operate in essentially the same fashion as discussed above for FIG. 3.

FIG. 7 shows an embodiment where one movable wall 44 includes flexible diaphragm 88. In this embodiment the motion of armature 38 and right pusher plate 32 is communicated to the left flexible diaphragm 88 by the heat transfer fluid 68 that also acts as a pressure transfer fluid. In this instance the heat transfer fluid has a dual purpose. The armature 38 includes heat pipe 90 as the armature extension. Heat pipes can have effective thermal conductivities several hundred times larger than a metal of the same cross-section. Heat from the motor is conducted through the heat pipe 90 to the movable wall 28 where it is transferred to the blood. Other operation characteristics are the same as FIG. 3.

FIG. 8 shows an embodiment where the armature 38 includes a single extension that is connected to piston 92. Both movable walls 28 and 44 include flexible diaphragms 88 and 94. The cavity 96, existing between right movable wall 28 and piston 92, is filled with heat transfer fluid 68. The motion of the armature and piston is communicated to both flexible diaphragms by the heat transfer fluid 68 that also acts as a pressure transfer fluid. In this instance the heat transfer fluid has a dual purpose. Other operation characteristics are the same as FIG. 3.

While the above description contains many specificities, these should not be construed as limitations on the scope of the invention, but rather as an exemplification of preferred embodiments. Other variations are possible. For example, many patients need not have a completely new heart but only a pump to assist their weak left ventricle. The invention may be adapted to provide an implantable left ventricular assist device. As another example the invention could be employed as a pump of general purpose. Accordingly, the scope of the invention should be determined not by the embodiments illustrated, but by the appended claims and their legal equivalents.

What is claimed is:

1. A totally implantable artificial heart comprising:
    (a) a central housing;
    (b) a linear electric motor enclosed within the central housing, comprising:
        (i) a stationary stator;
        (ii) an armature including a first armature end and a second armature end, the armature linearly movable along a longitudinal axis of the armature in response to an electric current provided to the motor, a linear operation of the electric motor producing thermal energy;
    (c) a right ventricle cavity forming a selectively variable right ventricle cavity volume for receiving and expelling blood, the right ventricle cavity comprising:
        (i) a right ventricle housing attached to the central housing;
        (ii) a first movable wall comprising a first pusher plate attached to the central housing by a first flexible seal and attached to the first armature end such that a linear motion of the armature causes the right ventricle cavity volume to change;
    (d) a first inlet port including a first inlet valve for allowing blood to enter the right ventricle cavity when the right ventricle cavity volume increases;
    (e) a first outlet port including a first outlet valve for allowing blood to exit the right ventricle cavity when the right ventricle cavity volume decreases;
    (f) a left ventricle cavity forming a selectively variable left ventricle cavity volume for receiving and expelling blood, the left ventricle cavity comprising:
        (i) a left ventricle housing attached to the central housing;
        (ii) a second movable wall comprising a second pusher plate attached to the central housing by a second flexible seal and attached to the second armature end such that the linear motion of the armature causes the left ventricle cavity volume to change;
    (g) a second inlet port including a second inlet valve for allowing blood to enter the left ventricle cavity when the left ventricle cavity volume increases;
    (h) a second outlet port including a second outlet valve for allowing blood to exit the left ventricle cavity when the left ventricle cavity volume decreases; and
    (i) heat transfer means for simultaneously conducting thermal energy from the electric motor to the first and second pusher plates, to the left and right ventricle housings, to the central housing, to blood that is being pumped through the artificial heart, and to body tissues surrounding the artificial heart.

2. The totally implantable artificial heart of claim 1 wherein the heat transfer means includes:
    (a) at least one flow passage selected from the group consisting of a flow passage over the stator, a flow passage through the stator, a flow passage through the armature, and a flow passage between the stator and the armature;
    (b) a heat transfer fluid; and
    (c) a plurality of heat transfer reservoir means for supplying heat transfer fluid to and receiving heat transfer fluid from at least one flow passage, the linear motion of the armature causing the heat transfer fluid to flow.

3. The totally implantable artificial heart of claim 2 wherein the at least one flow passage includes enhanced heat transfer surfaces.

4. The totally implantable artificial heart of claim 2 further comprising an impeller attached to the armature such that the linear motion of the armature sets the impeller in motion causing the heat transfer fluid to flow.

5. The totally implantable artificial heart of claim 1 wherein the heat transfer means further includes at least one heat conduction path selected from the group consisting of a heat conduction path through the armature, a heat conduction path through the first and second pusher plates, a heat conduction path from the stator to the right and left ventricle housings, and a heat conduction path from the stator to the central housing.

6. A totally implantable artificial heart comprising:
    (a) a central housing;
    (b) a linear electric motor enclosed within the central housing, comprising:
        (i) a stationary stator;
        (ii) an armature including an armature end, the armature linearly movable along a longitudinal axis of the armature in response to an electric current provided to the motor, an operation of the electric motor producing thermal energy;
    (c) a right ventricle cavity forming a selectively variable right ventricle cavity volume for receiving and expelling blood, the right ventricle cavity, comprising:
        (i) a right ventricle housing attached to the central housing;
        (ii) a first movable wall comprising a pusher plate attached to the central housing by a flexible seal and attached to the armature end such that a linear motion of the armature causes the first movable wall to move thereby causing the right ventricle cavity volume to change;
    (d) a first inlet port including a first inlet valve for allowing blood to enter the right ventricle cavity when the right ventricle cavity volume increases;
    (e) a first outlet port including a first outlet valve for allowing blood to exit the right ventricle cavity when the right ventricle cavity volume decreases;
    (f) a left ventricle cavity forming a selectively variable left ventricle cavity volume for receiving and expelling blood, the left ventricle cavity comprising:
        (i) a left ventricle housing attached to the central housing;
        (ii) a second movable wall comprising a flexible diaphragm;
    (g) a pressure transfer fluid for transferring pressure generated at the pusher plate to the flexible diaphragm, the pressure transfer fluid occupying a region formed by the pusher plate, the flexible seal, the central housing, and the flexible diaphragm, a motion of the pusher plate causing a motion of the diaphragm, resultantly causing the left ventricle cavity volume to change;
    (h) a second inlet port including a second inlet valve for allowing blood to enter the left ventricle cavity when the left ventricle cavity volume increases;
    (i) a second outlet port including a second outlet valve for allowing blood to exit the left ventricle cavity when the left ventricle cavity volume decreases; and (j) heat transfer means which includes the pressure transfer fluid for simultaneously conducting thermal energy from the electric motor to the first and second movable walls, to the left and right ventricle housings, to the central housing, to blood that is being pumped through the artificial heart, and to body tissues surrounding the artificial heart.

7. The totally implantable artificial heart of claim 6 wherein the heat transfer means includes:
   (a) at least one flow passage selected from the group consisting of a flow passage over the stator, a flow passage through the stator, a flow passage through the armature, and a flow passage between the stator and the armature;
   (b) a heat transfer fluid; and
   (c) a plurality of heat transfer reservoir means for supplying heat transfer fluid to and receiving heat transfer fluid from at least one flow passages, the linear motion of the armature causing the heat transfer fluid to flow.

8. The totally implantable artificial heart of claim 7 wherein the at least one flow passage includes enhanced heat transfer surfaces.

9. The totally implantable artificial heart of claim 7 further comprising an impeller attached to the armature such that the linear motion of the armature sets the impeller in motion causing the heat transfer fluid to flow.

10. The totally implantable artificial heart of claim 6 wherein the heat transfer means further includes at least one heat conduction path selected from the group consisting of a heat conduction path through the armature, a heat conduction path through the pusher plate, a heat conduction path from the stator to the right and left ventricle housings, and a heat conduction path from the stator to the central housing.

11. A totally implantable artificial heart comprising:
   (a) a central housing;
   (b) a linear electric motor enclosed within the central housing, comprising:
      (i) a stationary stator;
      (ii) an armature including an armature end, the armature linearly movable along a longitudinal axis of the armature in response to an electric current provided to the motor, an operation of the electric motor producing thermal energy;
   (c) a right ventricle cavity forming a selectively variable right ventricle cavity volume for receiving and expelling blood, the right ventricle cavity, comprising:
      (i) a right ventricle housing attached to the central housing;
      (ii) a first movable wall comprising a first flexible diaphragm, a motion of the first movable wall causing the right ventricle cavity volume to change;
   (d) a first inlet port including a first inlet valve for allowing blood to enter the right ventricle cavity when the right ventricle cavity volume increases;
   (e) a first outlet port including a first outlet valve for allowing blood to exit the right ventricle cavity when the right ventricle cavity volume decreases;
   (f) a left ventricle cavity forming a selectively variable left ventricle cavity volume for receiving and expelling blood, the left ventricle cavity comprising:
      (i) a left ventricle housing attached to the central housing;
      (ii) a second movable wall comprising a second flexible diaphragm, a motion of the second movable wall causing the left ventricle cavity volume to change;
   (g) a second inlet port including a second inlet valve for allowing blood to enter the left ventricle cavity when the left ventricle cavity volume increases;
   (h) a second outlet port including a second outlet valve for allowing blood to exit the left ventricle cavity when the left ventricle cavity volume decreases;
   (i) a movable piston attached to the armature;
   (j) a first pressure transfer fluid for transferring pressure generated by the movable piston to the first flexible diaphragm, the pressure transfer fluid occupying a first region formed by the movable piston, the first flexible diaphragm, and the central housing, a motion of the movable piston causing a motion of the first flexible diaphragm, resultantly causing the right ventricle cavity volume to change, the first pressure transfer fluid also facilitating the transfer of heat;
   (k) a second pressure transfer fluid for transferring pressure generated by the movable piston to the second flexible diaphragm, the pressure transfer fluid occupying a second region formed by the movable piston, the second flexible diaphragm, and the central housing, a motion of the movable piston causing a motion of the second flexible diaphragm, resultantly causing the left ventricle cavity volume to change the second pressure transfer fluid also facilitating the transfer of heat; and
   (l) heat transfer means for simultaneously conducting thermal energy from the electric motor to the first and second movable walls, to the left and right ventricle housings, to the central housing, to blood that is being pumped through the artificial heart, and to body tissues surrounding the artificial heart.

12. The totally implantable artificial heart of claim 11 wherein the heat transfer means includes:
   (a) at least one flow passage selected from the group consisting of a flow passage over the stator, a flow passage through the stator, a flow passage through the armature, and a flow passage between the stator and the armature;
   (b) a heat transfer fluid;
   (c) a plurality of heat transfer reservoir means for supplying heat transfer fluid to and receiving heat transfer fluid from at least one flow passages, the linear motion of the armature causing the heat transfer fluid to flow.

13. The totally implantable artificial heart of claim 12 wherein the at least one flow passage includes enhanced heat transfer surfaces.

14. The totally implantable artificial heart of claim 12 further comprising an impeller attached to the armature, such that a linear motion of the armature sets the impeller in motion thereby causing the heat transfer fluid to flow.

15. The totally implantable artificial heart of claim 11 wherein the heat transfer means further includes at least one heat conduction path selected from the group consisting of a heat conduction path through the armature, a heat conduction path through the pusher plate, a heat conduction path from the stator to the right and left ventricle housings, and a heat conduction path from the stator to the central housing.

* * * * *